United States Patent [19]

Dianis

[11] Patent Number: 5,262,575
[45] Date of Patent: Nov. 16, 1993

[54] PRODUCTION OF ALLYLIC CHLORIDES

[75] Inventor: William P. Dianis, Midland, Mich.

[73] Assignee: The Dow Chemical Company, Midland, Mich.

[21] Appl. No.: 925,342

[22] Filed: Aug. 4, 1992

[51] Int. Cl.$^5$ .............................................. C07C 17/00
[52] U.S. Cl. .................................... 570/235; 570/193
[58] Field of Search .................. 570/224, 235, 193

[56] References Cited

U.S. PATENT DOCUMENTS

| | | | |
|---|---|---|---|
| 2,966,525 | 12/1960 | Steen | 260/654 |
| 3,354,234 | 11/1967 | Hayden et al. | 269/656 |
| 3,462,501 | 8/1969 | Hornig et al. | 260/654 |
| 3,489,816 | 1/1970 | Hornig et al. | 260/654 |
| 3,513,207 | 5/1970 | Hornig et al. | 260/654 |
| 3,670,037 | 6/1972 | Dugan | 570/224 |
| 3,716,581 | 2/1973 | Calcagno | 560/243 |
| 3,855,321 | 12/1974 | Bach et al. | 260/654 R |
| 4,891,346 | 1/1990 | Hucul | 502/35 |

FOREIGN PATENT DOCUMENTS

| | | |
|---|---|---|
| 1960158 | 6/1971 | Fed. Rep. of Germany . |
| 8002023 | 10/1980 | PCT Int'l Appl. . |
| 363680 | 3/1973 | U.S.S.R. .............. 570/224 |
| 1104361 | 2/1968 | United Kingdom . |
| 1251535 | 10/1971 | United Kingdom . |
| 1252578 | 11/1971 | United Kingdom . |
| 1373296 | 11/1974 | United Kingdom . |

OTHER PUBLICATIONS

Fujimoto et al., "Oxychlorination of Propylene on Supported Palladium and Other Platinum Group Metal Catalysts," *Journal of Catalysis*, vol. 43, 234–242 (1976).

*Primary Examiner*—Howard T. Mars

[57] ABSTRACT

This invention, in one respect, is a process for producing allylic chlorides which comprises contacting a feedstream containing an olefin in the gas phase with a chlorination composition under conditions effective to produce an allylic chlorine and wherein the mole ratio of oxygen to olefin is from 0 to about 1:20 in the feedstream. The chlorination composition contains supported palladium chloride, platinum chloride, or palladium chloride and a chloride of a Group 1 alkali metal selected from the group consisting of lithium, sodium, and potassium; a Group 2 alkaline earth metal; a Group 9 metal; nickel; and a Group 12 metal. The chlorination composition can be regenerated by contacting the chlorination composition with chlorine in a cyclic reaction scheme.

In another respect, this invention is a composition consisting essentially of (A) palladium chloride, (B) a chloride of a metal selected from the group consisting of lithium, sodium, potassium, calcium, strontium, barium, nickel, and mixtures thereof, and (C) a support, wherein the weight percent of (A) and (B) in the composition is from about 0.1 to about 45.

23 Claims, No Drawings

PRODUCTION OF ALLYLIC CHLORIDES

BACKGROUND OF THE INVENTION

This invention relates to the production of olefinic chlorides, such as allyl chloride, from olefins having an allylic hydrogen by contacting the olefin with a chlorination composition.

Many processes are known for making allyl chloride. The known catalytic methods have not been used in commercial operation for a number of reasons including toxicity of the catalyst, cost of separating the products from the catalyst, cost of disposing of the solvent, production of undesirably high amounts of by-products, as well as less than desirable yields. For example, an oxychlorination is disclosed by Fujimoto et al. in *Journal of Catalysis*, Volume 43, pages 234–242 (1976) wherein oxygen, chlorine, and hydrogen chloride are contacted with propylene in the presence of a catalyst. It is noted by Fujimoto et al. at page 241, however, that when palladium chloride on carbon is the catalyst, the major product is 1,2-dichloropropane, not allyl chloride.

Hence, today, allyl chloride is produced by decades old technology wherein propylene and chlorine are reacted at high temperatures in the absence of catalyst. This process, however, is not without difficulties including production of undesirably high levels of polychlorinated by-products.

What is needed is an effective catalytic process to produce olefinic chlorides such as allyl chloride.

SUMMARY OF THE INVENTION

This invention, in one respect, is a process for producing allylic chlorides which comprises contacting a feedstream containing an olefin in the gas phase with a chlorination composition under conditions effective to produce an allylic chlorine and wherein the mole ratio of oxygen to olefin is from 0 to about 1:20 in the feedstream. This process can further comprise contacting the chlorination composition with chlorine in the absence of olefin under conditions effective to form palladium chloride.

In another respect, this invention is a composition for the production of allyl chloride from propylene, which consists essentially of (A) palladium chloride, (B) a chloride of a metal selected from the group consisting of lithium, sodium, potassium, calcium, strontium, barium, nickel, and mixtures thereof, and (C) a support, wherein the weight percent of (A) and (B) in the composition is from about 0.1 to about 45.

In another respect, this invention is a process for producing allyl chloride, which comprises (a) contacting a feedstream containing propylene in the gas phase with a chlorination composition in a moving bed reactor under conditions effective to form allyl chloride and wherein the mole ratio of oxygen to olefin is from 0 to about 1:20 in the feedstream, (b) separating the chlorination composition from the propylene feedstream and allyl chloride, (c) contacting the chlorination composition with chlorine in a second reactor under conditions effective to regenerate the chlorination composition, and (d) recycling the regenerated chlorination composition to Step (a).

Advantageously, a process practiced in accordance with this invention provides high conversion of olefins and high selectivity to allylic products. Moreover, this invention provides a process using a heterogeneous chlorination composition, thus eliminating separation of homogeneous catalyst from the products. This invention further provides a gas phase process wherein the olefin feed is substantially free of elemental oxygen in the production of allylic chlorides from olefins, unlike the prior art. Hence, the process of this invention for producing allylic chlorides is less prone to produce carbon dioxide from combustion of reactants due to the presence of elemental oxygen. This invention, moreover, results in higher conversions and selectivities to allylic products than was shown in oxychlorination processes of the prior art. This invention further provides a convenient step for regenerating a chlorination composition thereby facilitating a cyclic process scheme readily capable of commercialization.

DETAILED DESCRIPTION OF THE INVENTION

The olefins suitable for use in this invention have at least one allylic hydrogen. As defined herein, an "olefin" is represented by the formula $R^1R^2C=CR^3CHR^4R^5$ wherein $R^1$, $R^2$, $R^3$, $R^4$, and $R^5$ are independently in each occurrence hydrogen, aryl, or aliphatic group of from 1 to 6 carbon atoms, and any two of $R^1$, $R^2$, $R^3$, $R^4$, and $R^5$ may come together to form a cyclic ring. Useful olefins are gases under the conditions practiced in this invention. Examples of suitable aliphatic groups are branched or unbranched alkyls of from 1 to 6 carbon atoms and branched or unbranched alkenyls of from 1 to 6 carbon atoms. Examples of suitable aryl groups are phenyl, benzyl, alkylphenyl, and halophenyl. Preferred olefins are alkenes having from 3 to 6 carbon atoms. Examples of preferred olefins are propylene, butylene, pentylene, and hexylene. Most preferably, the olefin is propylene.

Hydrogen chloride can be employed as a diluent in the practice of this invention. The use of hydrogen chloride is optional, but is preferred. When hydrogen chloride is introduced as a component of the feedstream, the overall conversion to products other than 2-chloropropane increases with increasing amounts of hydrogen chloride. While selectivity to allylic chlorides decreases slightly with use of hydrogen chloride, the use of hydrogen chloride is beneficial. When present in the feedstream, the amount of hydrogen chloride can vary from greater than 0 to about 99 volume percent. Preferably, the amount of hydrogen chloride is greater than about 10 volume percent, more preferably greater than about 25 volume percent, and most preferably greater than about 40 volume percent. Preferably, the amount of hydrogen chloride is less than about 90 volume percent, more preferably less than about 85 volume percent, and most preferably less than about 75 volume percent.

Gases that are inert during the process can also be employed as diluents of the olefins. Examples of suitable inert gases are nitrogen, helium, argon, alkanes, and saturated chlorinated hydrocarbons. If an inert gas is employed in the process of this invention, the preferred inert gas is nitrogen. Similarly, by-products of the process such as saturated chlorinated hydrocarbons can be separated from products and then recycled back to the reactor, thus functioning as diluents in the reaction feed. The proportion of inert gas olefin employed in the feedstream can vary widely. Typically, when an inert gas is used, the amount of inert gas is greater than 0 and less than about 90 percent by volume in the feed. Preferably, the amount of inert gas employed is greater than 0 and less than about 50 percent by volume in the feed.

The process of this invention is conducted substantially in the absence of oxygen. That is, this process is not an oxychlorination. The presence of oxygen in this process leads to lower conversion and selectivity. In a typical oxychlorination process, oxygen and hydrogen chloride are present in the feedstream and serve to supply the chlorine for producing allylic chlorides. Similarly, about 1 mole of oxygen is employed per 2 moles of olefin and per 2 moles of hydrogen chloride in an oxychlorination. Conversely, in the process of this invention, the chlorination composition is the source of chlorine for producing allylic chlorides, and while hydrogen chloride can be used as a diluent in the process of this invention, the presence of oxygen is to be avoided. Thus, if oxygen is present, the mole ratio of oxygen to olefin is less than about 1:20, preferably less than 1:100. Similarly, in addition to the requirement for the oxygen to olefin mole ratio, the total amount of oxygen in the feedstream is less than about 3 volume percent, preferably less than about 1 volume percent.

As used herein, "chlorination composition" is a composition as defined hereinbelow.

One chlorination composition useful in this invention comprises palladium chloride ($PdCl_2$) on a support or a chloride of platinum such as $PtCl_2$, $PtCl_4$, or $H_2PtCl_6$ on a support. Suitable supports are described hereinbelow. Palladium chloride on a support is most preferred as the first chlorination composition useful in the practice of this invention. The amount of palladium or platinum chloride present on the support can be from about 0.1 percent by weight to about 20 percent by weight, preferably from about 2.5 percent by weight to about 10 percent by weight.

A second chlorination composition of this invention is a crystalline salt of palladium chloride and a second metal chloride. The second metal chloride can be a chloride of a Group 1 alkali metal selected from lithium, sodium, and potassium; a Group 2 alkaline earth metal; a Group 9 metal; nickel; and a Group 12 metals, on a support. Group numbers are as denoted by the current IUPAC notation as shown in *Hawley's Condensed Chemical Dictionary*, (Sax and Lewis rev. 11th ed. 1987). Preferably, the second metal chloride is a chloride of lithium, sodium, potassium, calcium, strontium, barium, or nickel. One or more of the second metal chlorides can be used. The amount of palladium chloride present on the support can be from about 0.1 percent by weight to about 20 percent by weight, preferably from about 2.5 percent by weight to about 10 percent by weight. Generally, the molar ratio of the second metal chloride to palladium chloride is less than or equal to about 2:1. When the valence of the second metal chloride is +1, the molar ratio of the second metal chloride to palladium chloride is preferably less than or equal to 2:1. When the valence of the second metal chloride is +2, the molar ratio of second metal chloride to palladium chloride is preferably less than or equal to 1.25:1. When the second metal chloride is potassium, the preferred molar ratio of potassium chloride to palladium chloride is about 1:2. Generally, the chlorination composition contains between about 0.1 and about 45 weight percent of total metal chlorides.

The supports useful in the first and second chlorination compositions of this invention can be any of the well known supports used in the art that have low adsorptive capacity toward reactants and products, sufficient strength for the particular reactor employed, and sufficient surface area. Examples of suitable supports are clay, base-exchanged or dealuminated zeolites, pumice, and combinations of silica and alumina of up to about 25 percent alumina by weight, silica gel, and crystalline forms of silica. Preferably, the support is silica gel or a combination of silica and alumina. Most preferably, the support is silica gel. The size of the final chlorination compositions can vary depending on the reactor configuration. For example, in a transport reactor the chlorination compositions of this invention typically have an average diameter of from about 50 micrometers to about 2000 micrometers, preferably from about 50 micrometers to about 1000 micrometers. In a fixed bed reactor, on the other hand, the chlorination compositions can be in the shape of extrudates up to one-quarter inch in diameter.

The chlorination composition of this invention can be prepared by methods well known to those skilled in this art. For example, the chlorination composition can be prepared by impregnation, ion-exchange, or vapor deposition. The preferred method is impregnation. Impregnation can be effected by dipping the support into an excess of a solution of the metal chlorides. Preferably, more precise control is achieved by a technique called "dry impregnation" or "impregnation to incipient wetness." In this method the support is treated with a quantity of the metal chloride solution corresponding to the total known pore volume of the support, or slightly less. The dry impregnation technique is described by Charles N. Satterfield in Heterogeneous Catalysis in Practice, McGraw-Hill Book Company, 1980, p. 82-83, and is incorporated herein by reference. Generally, the chlorination composition is prepared by adding palladium chloride or a mixture of palladium chloride and a second metal chloride to an amount of water sufficient to effect solution, heating or adding hydrogen chloride or both if necessary, and stirring the admixture to effect solution. Hydrogen chloride can be used to facilitate dissolution of the chloride salts, the amount of hydrogen chloride required being readily determined by those skilled in the art. Typically, the amount of hydrogen chloride used is about two molar equivalent relative to the metal chlorides. The solution is then contacted with a predetermined amount of support for sufficient time and in sufficient amount to effect impregnation of the support by any conventional technique such as those listed above. Finally, the support containing the impregnated metal chlorides is allowed to dry. Generally, drying is performed in air at from room temperature to about 110° C., but it can also be achieved in an inert atmosphere or using reduced pressure. The procedure used should be one which does not oxidize the metal chlorides, as is readily determined by those skilled in the art.

The process of this invention can be practiced in a variety of gas phase reactors, either batchwise or in a continuous manner. Examples of suitable reactors are fixed bed reactors, fluidized bed reactors, and moving bed reactors such as a riser reactor and a raining solids reactor. In a fixed bed reactor, the flow rate can be from about 10 to about 10,000 bed volumes per hour. In the cases of fixed bed or a fluidized bed reactors, however, the chlorination must be regenerated often by alternating streams of feed and chlorine. Such a scheme is less desirable than one wherein feed and fresh chlorination catalyst are continuously in contact. Thus, the most preferred reactor design suitable for the process of this invention is a moving bed reactor such as a riser reactor and a raining solids reactor. A moving bed reactor allows the chlorination composition to be contacted with the feed for short times followed by separating the feed from the chlorination composition. The chlorination composition can then be regenerated, as described hereinbelow, and returned to the entry point of chlorination composition in the moving bed reactor. Thus, fresh chlorination composition can be continuously contacted with the feed. In a riser reactor, the flow rate of feed varies widely depending on several factors such as size of the reactor and size of the chlorination composition. Generally, the flow rate is greater than the settling velocity of the chlorination catalyst and, thus, the flow rate is sufficient to move the chlorination composition upward but with the chlorination composition moving at a velocity less than the that of the feed. A suitable flow rate is readily ascertainable by a skilled artisan. At the top of the riser reactor, the reactants and products of the process are separated from the chlorination catalyst by conventional methods. Likewise, chlorination composition fines can be removed at this point or subsequent to the initial separation of chlorination composition. The products of the process can be separated by conventional methods such as by distillation.

The temperature at which this invention can be practiced is any temperature at which the olefin is converted to an allylic chloride. Generally, an effective temperature at which this invention can be practiced using the first chlorination composition is from about 200° C. to about 300° C. When the second chlorination composition is used in the practice of this invention, the temperature is from about 200° C. to about 350° C. Preferably, temperature using the first or second chlorination composition is from about 225° C. to about 275° C.

The pressure at which this invention can be practiced can be subatmospheric, superatmospheric, or atmospheric.

The desired products of the process are produced in high yield and high selectivity. It is understood that conversion will vary widely depending on several variables such as flow rate of reactants, activity of a particular chlorination composition, the properties of the reactants, and temperature. For purposes of this invention, "selectivity" is defined as the mole percentage of olefin converted to an olefin having a single allylic chlorine atom. For example, when propylene is the reactant, selectivity is measured by the mole percentage of propylene converted to allyl chloride. Generally, selectivity is greater than about 60 percent in the practice of this invention. Preferably, selectivity is greater than about 65 percent. In addition, the amount of polychlorinated products is low and the amount of carbon dioxide produced is negligible. For example, the yield of 1,2-dichloropropane is less than about 0.1 percent.

A minor by-product of the process of this invention is 2-chloropropane. Through thermodynamic calculations, it is now known that the amount of 2-chloropropane formed is determined by the thermodynamic equilibrium between propylene, HCl, and 2-chloropropane. Therefore, it is believed that if the feed contained an appropriate amount of 2-chloropropane, essentially no net formation of additional 2-chloropropane would take place. For example, when propylene conversion is 30 percent and the feedstream contains 100 percent propylene, it is calculated that 2 percent 2-chloropro-pane in the feedstream would result in essentially no net formation of 2-chloropropane. Alternatively, 2-chloropropane can be separated from allylic chloride product and by-products and heated to a temperature greater than about 350° C. to decompose 2-chloropropane to propylene and HCl. The propylene can be recycled into the feed.

In the course of producing allylic chlorides in the practice of this invention, chlorine is given up by the chlorination composition thereby inactivating it. For instance, if the chlorination composition is palladium chloride on a support, the chlorination composition becomes inactive when the palladium chloride has lost chlorine to yield elemental palladium (Pd°). The activity of the chlorination composition, or inactivated state thereof, can be readily determined by skilled artisans. The chlorination composition of this invention, therefore, requires regeneration to reform palladium chloride when the chlorination composition becomes inactive for production of allylic chlorides. Regeneration is accomplished by contacting the chlorination composition with elemental chlorine for a sufficient time and under conditions effective to substantially reform the palladium chloride. The amount of time will vary depending on several variables such as temperature, flow rate and concentration of elemental chlorine, and amount of chlorination composition to be regenerated. Preferably, the regeneration is performed in the absence of olefin. The elemental chlorine gas can be diluted with an inert carrier gas such as nitrogen, helium, carbon dioxide, and argon. Generally, regeneration is effected by contacting a chlorination composition with a moving force of gaseous elemental chlorine at a temperature of from about 200° C. to about 500° C. The elemental chlorine and chlorination composition are generally contacted for a time greater than 0 minutes and less than about 24 hours. At 300° C., under conditions wherein the rate of conversion of palladium to palladium chloride is not limited by the availability of chlorine or by the ability to remove the heat of reaction, the chlorination composition can be regenerated in about 30 minutes or less.

Alternatively, a chlorination composition is regenerated by contacting it with a moving force of a gas containing elemental oxygen and hydrogen chloride with the proviso that a molar excess of hydrogen chloride is used relative to the elemental oxygen. Contacting conditions are as described above for regeneration using elemental chlorine gas.

The regeneration can proceed in a number of alternative embodiments. For example, if a fixed bed reactor is employed, the chlorination composition can be regenerated by first ceasing to contact the olefin with the chlorination composition, typically by turning off the flow of olefin to the catalyst bed or by diverting the flow away from the chlorination composition bed, and next regenerating the chlorination composition. In addition, the chlorination composition can be removed from the fixed bed reactor and replaced with active chlorination composition, the removed chlorination composition being regenerated in a separate step outside of the reactor.

In a preferred embodiment in the case of a moving bed reactor, the chlorination composition is separated from the reactants and products after reaction. In a typical riser reactor, for example, reactants and a chlorination composition travel upward reaching the top where the reactor turns downward whereby the chlorination composition falls downward. Thus, a riser reactor can be envisioned as an upside down U-tube. As the chlorination composition falls, a stripping gas is often injected countercurrent to the falling chlorination composition. Hence, the reactants and products are separated from the catalyst. The stripping gas, reactants, and products thus move upward where they are removed from the riser reactor, typically through a port or aperture in the upper portion of the reactor. This port or aperture leads to one or more conventional apparatuses where the desired product is further separated from reactants and by-products, usually by distillation, condensation, adsorption, zone freezing, or combinations thereof. The separated chlorination composition is collected at the bottom of the riser reactor and is regenerated continuously or batchwise. The regenerated chlorination composition is then returned to the chlorination composition inlet of the riser reactor wherein it is again contacted with the reactant. The chlorination composition is thus repeatedly contacted with reactant, separated and collected, and regenerated. This is known as a cyclic process scheme.

The following examples are given to illustrate the invention and should not be interpreted as limiting it in any way. Unless stated otherwise, all parts and percentages are given by weight.

A riser reactor is simulated in a pulse microreactor which uses a very small volume of a chlorination composition. A microreactor is used to demonstrate that the desired reaction occurs and reveal the by-products. A riser reactor is also simulated in a conventional plug flow reactor that is operated in pulse mode. The volume of chlorination composition used for this apparatus is about 30 times larger than the microreactor. The pulse reactor can provide more performance information as the reaction proceeds, whereas the large apparatus tends to give a result that is the average of the data revealed in pulse microreactor. The pulse reactor is used to provide better indication of the selectivity one might expect in commercial equipment.

Compositions A and C–J each have a nominal weight percentage of $PdCl_2$ of about 5, or about 3 weight percent based on palladium metal only.

EXAMPLE 1

Preparation of Chlorination Compositions

Compositions A and B

Chlorination compositions are prepared by impregnating Davison 57 silica gel to incipient wetness with an aqueous solution of a noble metal halide. The chlorination compositions are dried at room temperature and then briefly at about 110° C. The composition of the solutions used for impregnation are tabulated below. In some cases the solutions are acidified with a few drops of HCl or heated or both to dissolve the salts. The chlorination composition prepared from palladium chloride is designated Composition A, while the chlorination composition prepared from platinum chloride is designated Composition B.

Composition C

Composition C, formally represented as $K_2PdCl_4$, is made by the following procedure. First, 0.135 gram of KCl is added to an aqueous solution of 2.8 grams deionized water and 0.2 gram concentrated HCl. Second, 0.16 gram of $PdCl_2$ is added to the above solution and is heated to about 60° C. until it dissolved. Finally, the above solution is used at room temperature to impregnate 1.25 grams of silica to incipient wetness.

| Salt | Amount Used (grams) | Total solution wt (grams) |
| --- | --- | --- |
| $PdCl_2$ | 0.0533 | 1.0292 |
| $H_2PtCl_6$ | 0.1640 | 1.1748 |

Compositions D–J

Compositions D–J are prepared by the following procedure. A stock solution is made by adding 3.3 grams of concentrated HCl to 46.7 grams of deionized water, adding 2.6667 grams (0.0150 moles) of $PdCl_2$ to the above solution ($3 \times 10^4$ moles/gram of solution), and stirring until dissolved, heating up to 60° C. if necessary.

Impregnating solutions to be added to the stock solution are prepared by adding a metal chloride to water to make about 1 gram of impregnating solution. The amounts of each metal chloride employed corresponds to the indicated molar ratios of metal chloride to palladium chloride. $CaCl_2$ and $BaCl_2$ are added as dehydrates. $NiCl_2$ and $SrCl_2$ are added as hexahydrates.

| Composition | Metal Chloride | Moles Metal Chloride/Mole $PdCl_2$ |
| --- | --- | --- |
| D | LiCl | 2.055 |
| E | NaCl | 2.076 |
| F | KCl | 0.505 |
| G | $CaCl_2$ | 1.049 |
| H | $NiCl_2$ | 1.079 |
| I | $BaCl_2$ | 1.079 |
| J | $SrCl_2$ | 1.087 |

The final solutions containing $PdCl_2$ and one of either LiCl, KCl, NaCl, $CaCl_2$, $NiCl_2$, $BaCl_2$, or $SrCl_2$ are each used to impregnate an appropriate amount of Davison 57 silica to incipient wetness. Generally, about 3 grams of impregnating solution is employed per 5 grams of silica. The impregnated silica is then dried at room temperature. The compositions so prepared are denoted herein as follows: Composition D is $2LiCl/PdCl_2$ on silica, Composition E is $2NaCl/PdCl_2$ on silica, Composition F is $0.5KCl/PdCl_2$, Composition G is $CaCl_2/PdCl_2$ on silica, Composition H is $NiCl_2/PdCl_2$ on silica, Composition I is $BaCl_2/PdCl_2$ on silica, and Composition J is $SrCl_2/PdCl_2$ on silica.

EXAMPLE 2

Preparation of Allyl Chloride Using Composition A in a Plug Flow Reactor

Twenty cc of Composition A is used in this example. The reactor is a 12 mm o.d. quartz tube with Composition A placed in the center third of the tube. Unimpregnated silica is used to pack the reactor tube above and below Composition A. The reactor is configured so that a regeneration of Composition A can be performed readily. The reactor is also configured so that the flow of propylene and helium can be changed intermittently. Prior to reaction, the reactor is purged with helium at room temperature for 10 minutes. Next, the reactor is heated at 5° C./minute to the desired temperature while maintaining a flow of helium through the reactor. After temperature is stabilized, the flow of helium is diverted from Composition A while simultaneously starting a flow of propylene over Composition A. The reactor effluent is collected in a sample bag that is inert to and substantially non-adsorptive of the effluent, such as a bag made of Teflon TM. The flow of propylene is continued for a time sufficiently long to deliver the desired volume of propylene at which time the flow of propylene is stopped and the flow of helium is simultaneously begun again. There is no oxygen present when propylene is contacted with Composition A. Effluent from the reaction is collected in the sample bag until all of the propylene or its reaction product is swept into the sample bag. The results of Example 1 are as follows in Table I for four runs.

TABLE I

|  | Run Number | | | |
|---|---|---|---|---|
|  | 1 | 2 | 3 | 4 |
| Temperature (°C.) | 250 | 250 | 275 | 275 |
| Propylene in feed (%) | 100 | 25 | 100 | 50 |
| Helium in feed (%) | 0 | 75 | 0 | 50 |
| Residence Time (sec) | 1.25 | 1.25 | 0.766 | 1.25 |
| Purge Helium (cc/min) | 540 | 540 | 840 | 258 |
| Propylene flow (cc/min) | 0 | 135 | 840 | 258 |
| Diluent Helium flow (cc/min) | 0 | 405 | 0 | 258 |
| Propylene Volume (cc) | 100 | 100 | 100 | 60 |
| Pulse Length (sec) | 11.11 | 44.44 | 7.14 | 13.95 |
| Conversion (%) | 35.1 | 33.7 | 37.9 | 57.1 |
| Selectivity to Allyl Chloride (%) | 73.0 | 84.0 | 77.1 | 80.6 |
| Selectivity to 2-chloropropane (%) | 17.5 | 6.6 | 9.9 | 5.4 |
| Selectivity to other by-products (%) | 9.5 | 9.4 | 13.0 | 13.9 |

It is seen in that in Table I, the selectivity to allyl chloride is very high, the amount of 2-chloropropane produced is relatively low, and the selectivity to other by-products such as 1,2-dichloropropane is also low.

EXAMPLE 3

Preparation of Allyl Chloride Using Composition A in a Pulse Microreactor

About 0.67 cc of Composition A is loaded into a pulse microreactor. Helium is flowed over Composition A at 30 ml/min. After the reactor is purged briefly at room temperature, the sample is heated to 225° C. A packed gc column being 30′×⅛″ with 20 percent bis ethoxy ethyl adipate on Chromosorb P acid washed is used to analyze the reactor effluent. A sample of propylene is caused to be injected into the helium carrier gas and then carried over Composition A. There is no oxygen in the feedstream which is contacted with Composition A. In this manner eight pulses of propylene are sent over Composition A. Each pulse contains about 0.203 cc of propylene. The effluent from each pulse is analyzed individually. Allyl chloride is detected in the first pulse, and the amount steadily increases, reaching a maximum in the third pulse, then declining. No allyl chloride is detected in the eighth pulse.

EXAMPLE 4

Preparation of Allyl Chloride Using Composition B in a Pulse Microreactor

Composition B in an amount of 0.67 cc is tested at 275° C. with a helium flow rate of about 30 cc/min. in a pulse microreactor. As in Example 2, propylene is caused to be injected into the helium carrier gas and then flowed over Composition B. Each pulse contains 0.125 cc of propylene. The reactor effluent is analyzed using a gc column being 30m×0.32 mm methylsilicone (J and W DB-1). Allyl chloride is detected as a product. The selectivity using Composition B is lower than with Composition A.

EXAMPLE 5

Preparation of Allyl Chloride Using Composition C in a Pulse Microreactor

The procedure of Example 3 is repeated except the chlorination composition is Composition C and the temperature is 225° C. A total of 10 pulses are directed over the chlorination composition. Allyl chloride is detected as a product with a selectivity similar to Composition A, but conversion is lower.

EXAMPLE 6

Preparation of Allyl Chloride Using Compositions D-J in a Plug Flow Reactor

The procedure of Example 2 is substantially repeated except Compositions D-J are employed. 20 cc of a given composition is loaded into the reactor which is operated at 275° C., residence time of 1.25 seconds, propylene flow of 515 cc/min., pulse length of 12.65 seconds, and helium purge flow rate of 515 cc/min. for 30.13 seconds.

The product is collected in a Teflon ™ gas sampling bag and is analyzed by capillary gc. The results of the tests are reported in Table II. Conversion and selectivity are expressed on a molar basis.

TABLE II

| Composition | Conversion (percent) | Selectivity to Allyl Chloride (percent) | Allyl Chloride Yield (percent) | 2-Chloropropane Selectivity (percent) | Others Selectivity (percent) |
|---|---|---|---|---|---|
| D | 39.8 | 74.0 | 29.4 | 8.6 | 17.4 |
| E | 32.7 | 72.9 | 23.8 | 11.4 | 15.6 |
| F | 38.8 | 76.6 | 29.7 | 9.1 | 14.2 |
| G | 38.5 | 68.7 | 26.5 | 11.1 | 20.2 |
| H | 33.6 | 72.4 | 24.4 | 11.6 | 16.0 |
| I | 34.4 | 71.4 | 24.5 | 15.7 | 13.0 |
| J | 25.3 | 76.6 | 19.4 | 14.3 | 9.1 |
| K | 36.5 | 76.8 | 28.0 | 12.6 | 10.6 |

It is seen in that in Table II, the selectivity to allyl chloride is very high, the amount of 2-chloropropane produced is relatively low, and the selectivity to other by-products such as 1,2-dichloropropane is also low.

EXAMPLE 7

Preparation of Allyl Chloride Using Composition A in a Plug Flow Reactor Using Various Amounts of Hydrogen Chloride in the Feedstream The procedure of Example 2 is substantially repeated except the feedstream contains hydrogen chloride in varying amounts. The results are reported in Table III.

TABLE III

| Run no. | Volume of propylene (cc) | HCl (%) | Conversion (%) | Selectivity to Allyl Chloride (percent) | Allyl Chloride Yield (percent) | 2-Chloro-propane Selectivity | Others Selectivity |
|---|---|---|---|---|---|---|---|
| 1 | 100 | 0 | 38.0 | 77.7 | 29.5 | 10.37 | 11.91 |
| 2 | 100 | 25 | 40.7 | 75.1 | 30.6 | 12.68 | 12.23 |
| 3 | 100 | 25 | 41.9 | 71.5 | 30.0 | 12.04 | 16.47 |
| 4 | 100 | 50 | 44.9 | 72.7 | 32.6 | 14.88 | 12.41 |
| 5 | 100 | 50 | 40.0 | 71.6 | 28.6 | 16.74 | 11.65 |
| 6 | 100 | 75 | 46.6 | 68.4 | 31.9 | 18.43 | 13.12 |
| 7 | 100 | 75 | 47.5 | 68.6 | 32.6 | 17.74 | 13.68 |
| 8 | 100 | 75 | 43.6 | 68.2 | 29.7 | 19.72 | 12.06 |
| 9 | 100 | 85 | 45.6 | 65.5 | 29.9 | 20.49 | 14.01 |
| 10 | 60 | 75 | 61.4 | 74.2 | 45.5 | 10.85 | 14.94 |
| 11 | 60 | 85 | 64.0 | 73.5 | 47.04 | 10.87 | 15.67 |

It is seen in Table III that increasing amounts of hydrogen chloride in the feedstream with propylene produces increased conversion under identical conditions. Selectivity to allyl chloride on the whole is not effected significantly by increasing amounts of hydrogen chloride.

EXAMPLE 8

Regeneration of Composition A

A fresh sample of Composition A is reacted with propylene to form allyl chloride, and next regenerated by exposing the composition to an atmosphere of 100 percent chlorine for 30 minutes at 300° C. The activity of the fresh and regenerated composition is reported below in Table IV. Prior to reaction of the regenerated composition, the reactor is purged of chlorine and the temperature is reduced to 275° C. The fresh and regenerated composition is reacted with propylene substantially in accordance with Example 2.

TABLE IV

| Run Number | Fresh | Regenerated |
|---|---|---|
| Temperature (°C.) | 275 | 275 |
| Propylene in feed (%) | 50 | 50 |
| Helium in feed (%) | 50 | 50 |
| Residence Time (sec) | 1.25 | 1.25 |
| Propylene Volume (cc) | 100 | 100 |
| Conversion (%) | 24.8 | 27.2 |
| Selectivity to Allyl Chloride (%) | 78.9 | 83.5 |
| Selectivity to 2-chloropropane (%) | 8.4 | 8.2 |
| Selectivity to other by-products (%) | 12.7 | 8.3 |

It is seen from Example 7 that the regeneration produces a very active composition which performs as well as fresh composition. In fact, in this example, the regenerated composition exhibits improved conversion, improved selectivity to allyl chloride, lower selectivity to 2-chloropropane, and lower selectivity to other by-products.

What is claimed is:

1. A process for producing allylic chlorides which comprises contacting a feedstream containing an olefin in the gas phase with a palladium chloride or platinum chloride containing chlorination composition under conditions effective to produce an allylic chloride and wherein the mole ratio of oxygen to olefin is from 0 to about 1:20 in the feedstream.

2. The process of claim 1 wherein the chlorination composition comprises palladium chloride on a support.

3. The process of claim 2 wherein the temperature is from about 200° C. to about 300° C.

4. The process of claim 1 wherein the chlorination composition comprises palladium chloride and a second metal chloride selected from the group consisting of chlorides of a Group 1 alkali metal selected from the group consisting of lithium, sodium, and potassium; a Group 2 alkaline earth metal; a Group 9 metal; nickel; and a Group 12 metal; on a support.

5. The process of claim 4 wherein the second metal chloride is a chloride of lithium, sodium, potassium, calcium, strontium, barium, or nickel.

6. The process of claim 4 wherein the temperature is from about 200° C. to about 350° C.

7. The process of claim 1 wherein the temperature is from about 225° C. to about 275° C.

8. The process of claim 1 wherein the process is conducted in a moving bed reactor.

9. The process of claim 8 wherein the process is conducted in a riser reactor.

10. The process of claim 1 wherein the olefin is propylene, butylene, pentylene, or hexylene.

11. The process of claim 11 wherein the olefin is propylene and the allylic chloride is allyl chloride.

12. The process of claim 11 wherein the selectivity is greater than or equal to about 60 percent.

13. The process of claim 1 wherein the mole ratio of oxygen to olefin is from 0 to about 1:100.

14. The process of claim 1 which further comprises contacting the chlorination composition with chlorine in the absence of olefin under conditions effective to form palladium chloride.

15. A process for producing allyl chloride, which comprises (a) contacting a feedstream containing propylene in the gas phase with a palladium chloride or platinum chloride containing chlorination composition in a moving bed reactor under conditions effective to form allyl chloride and wherein the mole ratio of oxygen to olefin is from 0 to about 1:20 in the feedstream, (b) separating the chlorination composition from the propylene feedstream and allyl chloride, (c) contacting the chlorination composition with chlorine in a second reactor under conditions effective to regenerate the chlorination composition, and (d) recycling the regenerated chlorination composition to Step (a).

16. The process of claim 15 wherein the chlorination composition comprises palladium chloride on a support.

17. The process of claim 16 wherein the temperature is from about 200° C. to about 300° C.

18. The process of claim 15 wherein the chlorination composition comprises palladium chloride and a second metal chloride selected from the group consisting of chlorides of a Group 1 alkali metal selected from the group consisting of lithium, sodium, and potassium; a Group 2 alkaline earth metal; a Group 9 metal; nickel; and a Group 12 metal; on a support.

19. The process of claim 18 wherein the second metal chloride is a chloride of lithium, sodium, potassium, calcium, strontium, barium, or nickel.

20. The process of claim 18 wherein the temperature is from about 200° C. to about 350° C.

21. The process of claim 15 wherein the temperature is from about 225° C. to about 275° C.

22. The process of claim 15 wherein the process is conducted in a riser reactor.

23. The process of claim 15 wherein the selectivity is greater than or equal to about 60 percent.

* * * * *